(12) United States Patent
MacDougall et al.

(10) Patent No.: US 11,801,395 B2
(45) Date of Patent: Oct. 31, 2023

(54) OPTICAL APPLICATOR FEATURE OPTIMIZER

(71) Applicant: Lumeda Inc., Rocky Hill, CT (US)

(72) Inventors: Trevor MacDougall, South Dartmouth, MA (US); Sanders Paul, Madison, CT (US)

(73) Assignee: Lumeda Inc., Rocky Hill, CT (US)

( * ) Notice: Subject to any disclaimer, the term of this patent is extended or adjusted under 35 U.S.C. 154(b) by 0 days.

(21) Appl. No.: 17/597,657

(22) PCT Filed: Jul. 28, 2021

(86) PCT No.: PCT/US2021/043451
§ 371 (c)(1),
(2) Date: Jan. 13, 2023

(87) PCT Pub. No.: WO2023/009110
PCT Pub. Date: Feb. 2, 2023

(65) Prior Publication Data
US 2023/0191147 A1    Jun. 22, 2023

(51) Int. Cl.
*A61N 5/06* (2006.01)

(52) U.S. Cl.
CPC ........... *A61N 5/062* (2013.01); *A61N 5/0601* (2013.01); *A61N 2005/063* (2013.01); *A61N 2005/0627* (2013.01)

(58) Field of Classification Search
CPC ............. A61N 5/06; A61N 5/0601; A61N 2005/0602; A61N 5/063; A61N 5/062; A61N 2005/0626; A61N 2005/0627; A61N 2005/063; A61N 2005/065; A61N 2005/0658; A61N 2005/0662; A61N 5/067
USPC ................................................ 607/88, 89, 93
See application file for complete search history.

(56) References Cited

U.S. PATENT DOCUMENTS

| | | | | |
|---|---|---|---|---|
| 6,011,563 A | * | 1/2000 | Fournier | A61N 5/062 378/65 |
| 2005/0251230 A1 | | 11/2005 | MacKinnon et al. | |
| 2011/0034971 A1 | * | 2/2011 | Svanberg | A61N 5/0601 607/88 |
| 2012/0065494 A1 | * | 3/2012 | Gertner | A61B 8/06 601/2 |
| 2012/0184495 A1 | * | 7/2012 | Koyakutty | B82Y 5/00 977/773 |
| 2020/0246179 A1 | * | 8/2020 | Peyman | A61K 9/51 |

* cited by examiner

*Primary Examiner* — Ahmed M Farah
(74) *Attorney, Agent, or Firm* — Matthew J Patterson

(57) ABSTRACT

A photodynamic therapy (PDT) apparatus and method are disclosed. The PDT apparatus can include a flexible optical applicator that includes a plurality of light emitting devices for producing an irradiance pattern of therapy light to a target area of a patient. The PDT system includes an optical light controller that includes a computer processor. The method disclosed includes determining a treatment plan based on a plurality of therapy light parameters, photosensitizing drug selection, patient specific parameters, optimized light interval and other relevant parameters. The method further includes monitoring the application of the therapy light against the treatment plan and determining an updated treat plan in the event of a deviation from an initial treatment plan.

12 Claims, 5 Drawing Sheets

OPTICAL APPLICATOR FEATURE OPTIMIZER

CROSS REFERENCE TO RELATED APPLICATIONS

This application claims the benefit of Patent Cooperation Treaty Patent Application Serial No PCT/US21/43451 filed 28 Jul. 2021. The disclosure of the application above is incorporated herein by reference in its entirety.

BACKGROUND OF THE INVENTION

Field of the Invention

The present disclosure relates to photodynamic therapy.

Description of the Related Art

Light therapy can be used for treatment of conditions in multiple ways. For example, some light therapies involve the delivery of a therapeutic light through a fiber optic device placed proximal to or within a target tumor or cancerous tissue.

Some prior art light therapies can be combined with prior administration of light sensitive medicine (i.e., photosensitizer) that absorbs the therapeutic light and interacts with surrounding tissue constituents (e.g., oxygen) to generate reactive species that can destroy the target tissue. This form of therapy is known as photodynamic therapy ("PDT"). PDT uses light (such as light provided by a laser) to activate the photosensitizer. The process can work in three different ways: it destroys cancer cells, shuts down blood vessels that "feed" the tumor, and prompts the immune system to kill cancer cells throughout the body. It is associated with mild side effects and can be combined with standard chemotherapy and surgery and followed with radiation therapy. The most common prior art PDT method uses a single optical fiber to administer light for a particular photosensitizer, in which the wait time for a particular photosensitizer is specified for a particular indication in the prescribing information for the photosensitizer drug. Depending on the particular drug, different light instruments may be needed to match the required irradiance level.

The examples of the prior art lack the ability to provide a known amount of light dosage to an entire surface of a tumor in a fast and efficient way. For at least the reasons stated herein before, it is desirable to provide light therapy device and method that alleviates the known problems.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an. The optical light delivery system also includes a light source, a detector configured to receive light from the light source and to output a detection signal, a computer processor electrically coupled to the light source and the detector and configured to determine at least one parameter of the light source from the detection signal, and a light source controller electrically coupled to the computer processor and the light source and configured to control the light source based at least in part on the at least one parameter. Other embodiments of this aspect include corresponding computer systems, apparatus, and computer programs recorded on one or more computer storage devices, each configured to perform the actions of the methods.

Implementations may include one or more of the following features. The optical light delivery system where the computer processor is further configured to receive user input and where the light source controller is further configured to control the light source based on the user input and the at least one parameter. The user input is at least any of a photosensitizing drug type, a treatment type and a tissue type. The at least one parameter of the light source is any of a nominal peak wavelength, a fluence, a duty cycle and a fluence rate. The photosensitizing drug type is selected from the group may include porfimer (PHOTOFRIN®), talaporfin sodium (Laserphyrin®), 2-(1-Hexyloxyethyl)-2-Devinyl Pyropheophorbide-a (HPPH-Photochlor), benzoporphyrin derivative monoacid ring A (Verteporfin, Visudyne®), redaporfin (LUZ11), chlorin E6/P6/purpurin (Bremachlorin®, Radachlorin®), Ru(II) polypyridyl complex (TLD-1433), padeliporfin di-potassium (TOOKAD®) and 5-aminolevulinic acid hydrochloride (Gliolan™, 5-ALA). The photosensitizing drug type may include 2-(1-hexyloxyethyl)-2-devinyl pyropheophorbide-a and the light source controller is configured to control the light source to output light at a nominal peak wavelength of 665 nm. The photosensitizing drug type may include porfimer sodium and the light source controller is configured to control the light source to output light at a nominal peak wavelength of 630 nm. The photosensitizing drug type may include talaporfin and the light source controller is configured to control the light source to output light at a nominal peak wavelength of 664 nm. The photosensitizing drug type may include 5-aminolevulinic acid and the light source controller is configured to control the light source to output light at a nominal peak wavelength of 630 nm. The photosensitizing drug type has a prescribed activation peak wavelength and where the light source controller is configured to control the light source to output light at a nominal peak wavelength substantially centered about the prescribed activation peak wavelength. The treatment type is selected from the group may include of necrotic, apoptotic, vascular and immunogenicity. The user input further may include any of a starting nominal peak wavelength, a starting fluence, a starting fluence rate, a starting time and a starting run time. The optical light delivery system is configured to treat a tissue of a patient and where the computer processor is configured to drive the light source controller to treat the tissue of the patient in a closed loop fashion. The light source is configured to deliver the light to the tissue of the patient using a surface contact device or an interstitial device. The light source may include a tunable light source and the light source controller is configured to control the light source within a predetermined wavelength band of light. The computer processor is configured to monitor the detection signal. Implementations of the described techniques may include hardware, a method or process, or computer software on a computer-accessible medium.

One general aspect includes a method of delivering a therapy light to a tissue of a patient. The method also includes providing a configurable photodynamic therapy system having a light emitting device, selecting a treatment type, selecting a photosensitizing drug, determining a plurality of parameters of the therapy light in accordance with the treatment type and the photosensitizing drug, determining an initial treatment plan based on the plurality of parameters of the therapy light, administering the photosensitizing drug to the patient, and delivering the therapy light to the tissue in accordance with the initial treatment plan. Other embodiments of this aspect include corresponding computer systems, apparatus, and computer programs recorded on one or more computer storage devices, each configured to perform the actions of the methods.

Implementations may include one or more of the following features. The method may include obtaining a digital image of a target area of the tissue, and where the determining the plurality of parameters of the therapy light includes determining an irradiance pattern using the light emitting device and where the irradiance pattern substantially matches the digital image. The method may include positioning the light emitting device using the digital image of the target area of the tissue. The light emitting device may include a surface contact device and where the surface contact device is positioned against the target tissue. The determining the initial treatment plan further includes the optimum drug-light delivery interval. The method may include monitoring the therapy light and comparing the therapy light to the initial treatment plan, producing a difference between the therapy light and the initial treatment plan, determining an updated treatment plan based on the difference, and delivering the therapy light to the tissue in accordance with the updated treatment plan. The photosensitizing drug includes a prescribed activation peak wavelength and where the delivering the therapy light to the tissue may include controlling a light source to output the therapy light at a nominal peak wavelength substantially centered about the prescribed activation peak wavelength. The photosensitizing drug may include 2-(1-hexyloxyethyl)-2-devinyl pyropheophorbide-a and controlling the light source to output the therapy light substantially centered about a nominal peak wavelength of 665 nm. The photosensitizing drug type may include porfimer sodium and controlling the light source to output the therapy light substantially centered about a nominal peak wavelength of 630 nm. The photosensitizing drug type may include talaporfin and the controlling the light source to output the therapy light substantially centered about a nominal peak wavelength of 664 nm. The photosensitizing drug type may include 5-aminolevulinic acid and controlling the light source to output the therapy light substantially centered about a nominal peak wavelength of 630 nm. The determining the initial treatment plan further includes determining a duty cycle of the light emitting device. The determining the initial treatment plan further includes determining a fluence and a fluence rate of the light emitting device. The selecting a treatment type includes selecting from the group may include of necrotic, apoptotic, vascular and immunogenicity. The method of delivering a therapy light to a tissue of a patient is a part of an intraoperative procedure. Implementations of the described techniques may include hardware, a method or process, or computer software on a computer-accessible medium.

One general aspect includes a processor-implemented method to deliver a therapy light to a tissue of a patient. The processor-implemented method also includes administering a photosensitizing drug to the patient, acquiring a preprocedural image of a surgical site, where the preprocedural image includes a first marker and a target tissue, providing a configurable photodynamic therapy system having a processor and a light emitting device, where the light emitting device includes a second marker, positioning the light emitting device against the target tissue with the second marker proximate the first marker, acquiring an intraprocedural image of the surgical site, where the intraprocedural image includes the first marker and the second marker, aligning the first marker and the second marker using the intraprocedural image, where aligning may include determining a distance between the first marker and the second marker and moving the light emitting device the distance to align the first mark and the second marker, and using the processor, selecting a treatment type, selecting the photosensitizing drug, determining a plurality of parameters of the therapy light in accordance with the treatment type and the photosensitizing drug, determining an initial treatment plan based on the plurality of parameters of the therapy light, and delivering the therapy light to the target tissue in accordance with the initial treatment plan. Other embodiments of this aspect include corresponding computer systems, apparatus, and computer programs recorded on one or more computer storage devices, each configured to perform the actions of the methods.

Implementations may include one or more of the following features. The processor-implemented method where the determining the plurality of parameters of the therapy light includes determining an irradiance pattern using the light emitting device and where the irradiance pattern substantially matches either the preprocedural image or the intraprocedural image. The determining the initial treatment plan further includes the optimum drug-light delivery interval. Implementations of the described techniques may include hardware, a method or process, or computer software on a computer-accessible medium.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

A light delivery system capable of delivering a controlled dose of light irradiance over a wide range of irradiance values, to a biological target containing a photosensitizing drug at an optimal drug-light interval to elicit optimum PDT effects is disclosed.

Figure 1:
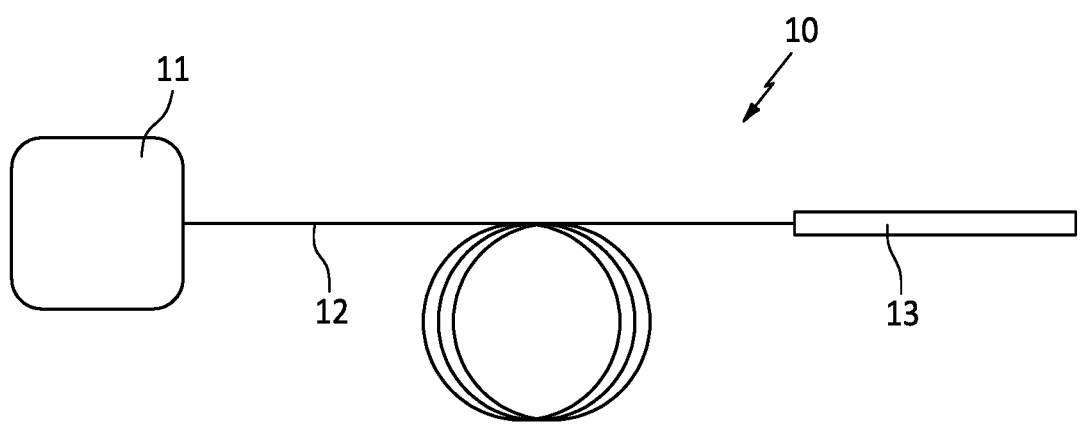
FIG. 1 is a schematic view of a configurable PDT system in accordance the present disclosure.

It has been shown in clinical studies that the application of Photo-Dynamic Therapy (PDT) to cancer tissue will enhance its response to immuno-therapy treatments. Heretofore it has not been possible to match the treatment of the PDT to the optimal conditions of position of the photosensitizer (photosensitizing) within the cell structure. After the photosensitizing is administered, a typical wait time of 24-48 hours is required using prior art methods to for the photosensitizing to leave the healthy cells, generally through vascular effects. As will be described in more detail herein after, a more focused and direct light application can be used to avoid healthy cells. In addition, the PDT could be applied earlier than 24-48 hours which can be a more optimum time to ensure the highest immune therapy success. Also, dose rate (measure in mW/cm2) must be precisely controlled at a relatively lower rate than other PDT applications. In the prior art PDT is applied using either a constant dose rate single cylindrical light diffuser (CLD) or optical surface applicator (OSA). With reference to FIG. 1, there is shown an optical light delivery system in the form of a configurable PDT system 10 of the present disclosure that includes optical control instrument 11, optical cable 12 and optical delivery device 13. In certain embodiments optical control instrument 11 includes at least one computer processor, a light source, a light source controller and various inputs and outputs including those to optically couple the optical control instrument to optical cable 12. The light source can comprise a source configured to produce therapy light at a single wavelength, a plurality of sources each configured to produce therapy light at a different respective wavelength, or a tunable source configured to produce therapy light at a different respective wavelength or predetermined wavelength band. The light source controller is configured to control the duty cycle and the power output of the light source, among other things. Optical delivery device 13 includes a light emitter which can comprise various devices including a CLD configured to be optically couple to optical cable 12 and to deliver therapy light from the light source in optical control instrument 11 to a patient as will be disclosed in more detail herein after. Optical delivery device 13 can also include a fiber detector configured to detect light emitted from the optical delivery device. Optical cable 12 comprises any number of optical fibers including a delivery fiber optically coupled to the emitter and a collecting fiber optically couped to the detector fiber. Now with reference to FIG. 2, there is shown a configurable PDT system 20 of the present disclosure that includes optical control instrument 21, optical cable 22 and optical delivery device 23. In certain embodiments optical control instrument 21 includes at least one computer processor, a light source, a light source controller and various inputs and outputs including those to optically couple the optical control instrument to optical cable 12. The light source can comprise a source configured to produce therapy light at a single wavelength, a plurality of sources each configured to produce therapy light at a single wavelength, a plurality of sources each configured to produce therapy light at a different respective wavelength, or a tunable source configured to produce therapy light at a different respective wavelength. The light source controller is configured to control the duty cycle and the power output of the light source, among other things. Optical delivery device 23 is surface contact device in the form of an optical applicator which includes a plurality of light emitters which can be comprised of various devices including a plurality CLDs positioned within the optical applicator, and each configured to be optically couple to optical cable 12 and to deliver therapy light from the light source(s) in optical control instrument 11 to a patient as will be disclosed in more detail herein after. Optical delivery device 23 can also include a plurality of fiber detectors configured to detect light emitted from the plurality of light emitters. Optical cable 22 comprises any number of optical fibers including a plurality of delivery fibers optically with each optically coupled to one of the light emitters and a plurality of collecting fibers optically with each optically coupled to one of the detector fibers.

Figure 3:
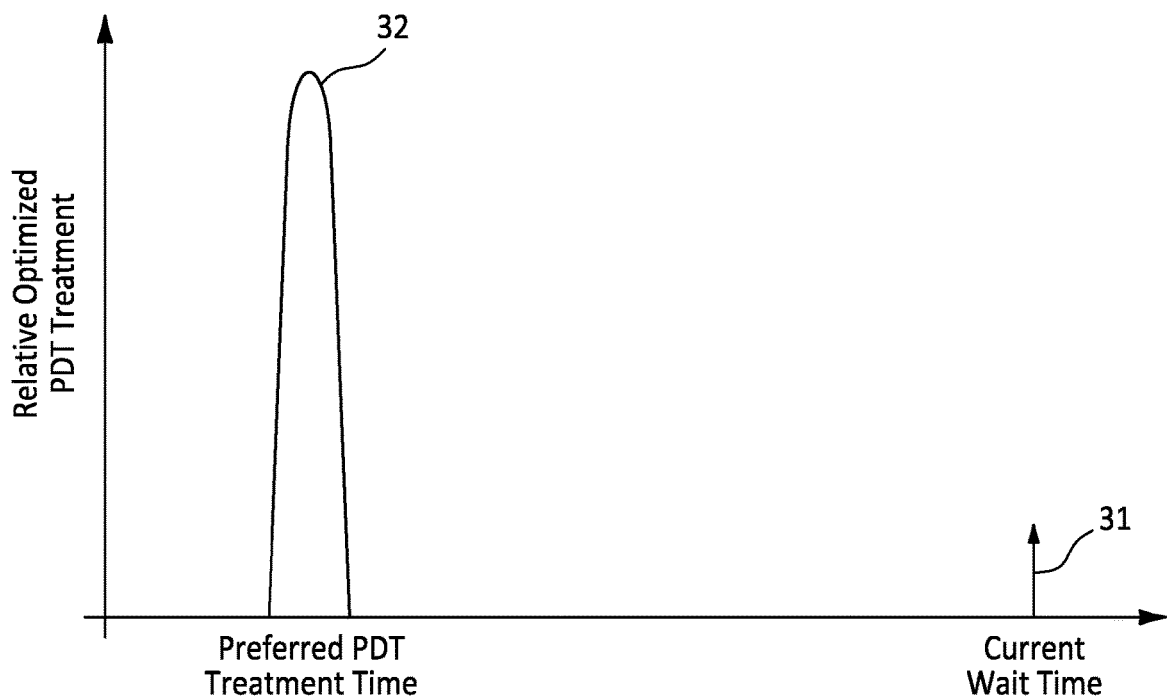
FIG. 3 is a graphical representation of optimum drug-light interval of a configurable PDT system in accordance the present disclosure.

It is known that PDT elicits oxidative cell death via necrotic or apoptotic effects. Studies have shown that the application of PDT can cause or enhance antitumor immune response. These effects are dependent on multiple factors such as type of photosensitizer, its localization, light dose and rate of exposure, and cell genotype. As will be disclosed hereinafter, PDT light delivery of the current disclosure are able to precisely focus on target tissue of a patient that avoids healthy tissue. This discovery has enabled a method that can allow more flexibility to apply PDT at an optimum drug-light interval (DLI). DLI as used herein is defined as the time of light administration after photosensitizing drug administration. The optimum DLI is selected to elicit certain therapeutic effects. Heretofore there does not exist a light instrument capable of delivering a controlled dose of light irradiance over a wide range of irradiance values, to a biological target containing a photosensitizing drug at an optimal DLI to elicit optimum PDT effects. The DLI is depicted graphically with reference to FIG. 3 wherein DLI is shown on the abscissa and the optimized PDT treatment is shown on the ordinate. Relative PDT treatment 31 depicts the prior art wherein DLI is 24-48 hours (although shown at a single time for simplicity) and the relative optimization is low. As part of the present disclosure, optimized window 32, having a DLI ranging from minutes to a few hours, shows a dramatically higher relative optimized PDT treatment effect. One of the reasons that the optimized PDT treatment effect at DLI optimized window 32 is higher is because more of the photosensitizing is present in the cancerous cells of the target area because it hasn't dissipated due to vascular and other known effects. Another reason that the optimized PDT treatment effect at DLI optimized window 32 is higher is because it can trigger an enhancement of the immune-response with the presence of higher photosensitizing concentrations.

Figure 2:
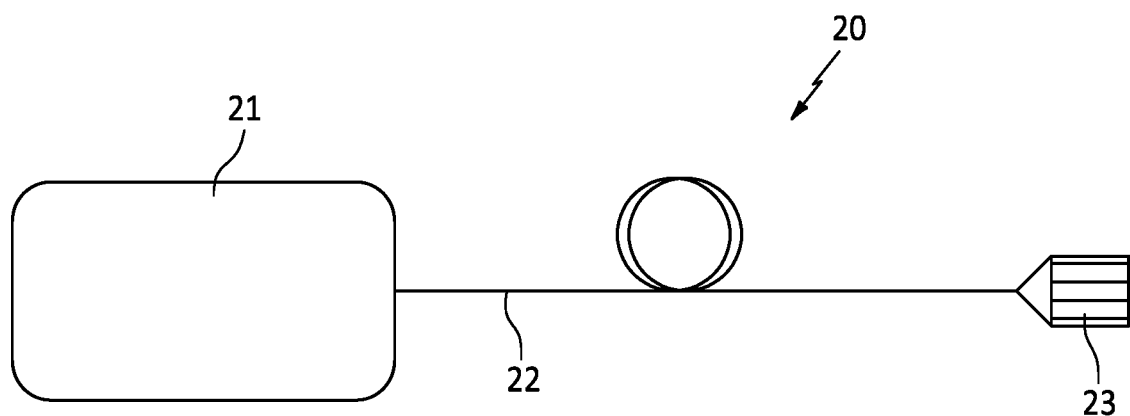
FIG. 2 is a schematic view of a configurable PDT system in accordance the present disclosure.

Referring to FIG. 2, configurable PDT system 20, using methods disclosed herein, includes the use of optical control instrument 21 and optical applicator 23 to apply an accurately focused therapy light on targeted cancer tissue at precise dose rates. In embodiments of the present disclosure, dose rates, also referred to herein as fluence rates, can be tuned to provide the optimum average dose rate as measured in $mW/cm^2$ at a chosen DLI to optimize the chemical process of enhancing the cancer cells to more fully respond to immune-therapy treatment.

Figure 4:
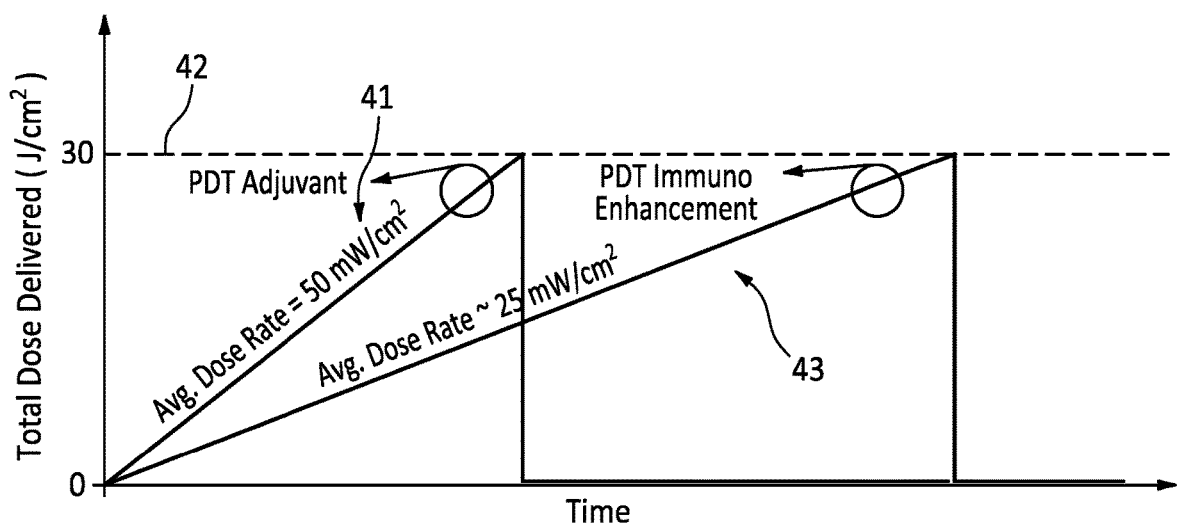
FIG. 4 is a graphical representation of dose rates of a configurable PDT system in accordance the present disclosure.

Referring now to FIG. 4, there is shown a graphical representation 40 of two different example PDT treatment types enabled by configurable PDT system 20 of the present disclosure. Although only two treatment examples are detailed, the configurable PDT system 20 is not limited to such treatment types and those skilled in the art should recognize that many different treatment types are contemplated by the present disclosure. In the first instance, a PDT adjuvant treatment 41 is shown that can be administered to a target area after surgical removal of a tumor. PDT adjuvant treatment 41 can be applied to suppress secondary tumor formation, typically adjuvant treatment is recommended after a relatively longer DLI. In this example, optical control instrument 21 controls the light source to provide PDT adjuvant treatment 41 with therapy light to a target area at a fluence, or dose rate, of 50 mW/cm$^2$ for approximately 10 minutes to achieve a total dose 42 of 30 J/cm$^2$. As will be discussed in more detail herein after, the total area of exposure is controlled by optical control instrument 21 in accordance with a treatment plan to precisely target specific cancerous tissue while avoiding exposing healthy tissue. Also shown in graphical representation 40 is PDT immuno-enhancement treatment 43. As disclosed herein before, PDT immuno-enhancement treatment 43 can be applied to trigger an enhancement of the immune-response with the presence of higher photosensitizing concentrations when such treatment is enacted with a short DLI. In this example, optical control instrument 21 controls the light source to provide PDT immuno-enhancement treatment 43 with therapy light to a target area at a fluence, or dose rate, of 25 mW/cm$^2$ for approximately 20 minutes to achieve a total dose 42 of 30 J/cm$^2$. As with PDT adjuvant treatment 41, the total area of exposure is controlled by optical control instrument 21 in accordance with a treatment plan to precisely target specific cancerous tissue while avoiding exposing healthy tissue. It should be appreciated by those skilled in the art that the ability to precisely target the cancerous tissue is critical during a PDT immuno-enhancement treatment 43 because the surrounding healthy tissue will contain higher photosensitizing concentrations than prior art PDT methods.

Figure 5:
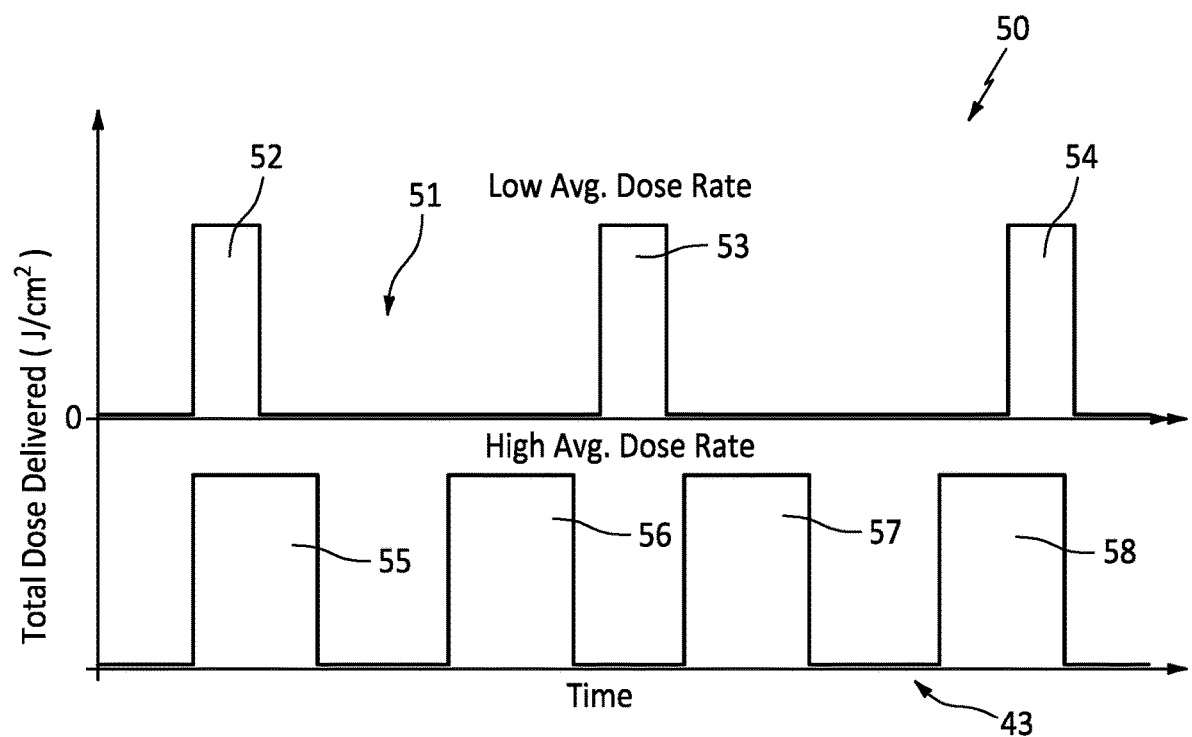
FIG. 5 is a graphical representation of light modulation schemes of a configurable PDT system in accordance the present disclosure.

Referring now to FIG. 5, there is shown a graphical representation 50 of two different example duty cycles for delivering modulated therapy light to a target area enabled by configurable PDT system 20 of the present disclosure. Although only two example duty cycles are detailed, the configurable PDT system 20 is not limited in the type and number of duty cycles and those skilled in the art should recognize that many different duty cycles are contemplated by the present disclosure. In order to control the average dose rate being applied by configurable PDT system 20 a duty cycle modulation technique can be applied. As discussed herein above related to PDT adjuvant treatment 41 and for immuno-enhancement treatment 43, different duty cycles can be applied to provide for different treatment types. Low average dose duty cycle 51 is comprised of three on cycles 52, 53, 54 with off (dwell) times occurring in between. Optical control instrument 21 controls the light source to produce the fluence rate for the on/off cycles in accordance with a treatment plan to provide a total dose at the completion of the duty cycle low average dose duty cycle 51. Also shown is high average dose duty cycle 51 is comprised of four on cycles 55, 56, 57, 58 with off (dwell) times occurring in between. Optical control instrument 21 controls the light source to produce the fluence rate for the on/off cycles in accordance with a treatment plan to provide a total dose at the completion of the high average dose duty cycle 58. In addition to duty cycle modulation, the computer processor of optical control instrument 21 can be programmed to apply any recipe of PDT dose rate to optimize the adjuvant treatment and enhancement of the immune-response.

With reference back to FIG. 2 there is shown configurable PDT system 20. The light controller of optical control instrument 21 is configured to measure irradiance (both irradiance pattern and fluence rate) delivered by the plurality of light emitters as well as being configured to output a wide range of fluence rates from 5 mW/cm$^2$ to 300 mW/cm$^2$. As disclosed herein above, configurable PDT system 20 is further configured to modulate these fluence rates, and direct light to targeted tissue using optical delivery device 23 in the form of a conformable surface applicator as well as other light diffusing devices that enables a desired spatial profile across the device. The optical delivery device 23 of configurable PDT system 20 is particularly suited for use within a body of a patient during an interoperative procedure. Other embodiments include interstitial devices. The plurality of light emitters and the light controller enables highly controllable irradiance patterns such that therapy light can be applied precisely to a target area of interest. These attributes of configurable PDT system 20 enables a method of treatment having a short DLI to elicit a prescribed treatment response as disclosed herein above. As disclosed herein above, in certain embodiments the light source of configurable PDT system 20 can comprise a source configured to produce therapy light various wavelengths and include a plurality of sources each configured to produce therapy light at a different respective wavelength, or a tunable source configured to produce therapy light at a different respective wavelength. The ability to produce therapy light at various wavelengths advantageously enables configurable PDT system 20 to be used with a wide range of photosensitizing drugs having different prescribed wavelength triggers. The various photosensitizing drugs for which configurable PDT system 20 is suitable include sodium porfimer (PHOTOFRIN®), talaporfin sodium (Laserphyrin®), 2-(1-Hexyloxyethyl)-2-Devinyl Pyropheophorbide-a (HPPH-Photochlor), benzoporphyrin derivative monoacid ring A (Verteporfin, Visudyne®), redaporfin (LUZ11), chlorin E6/P6/purpurin (Bremachlorin®, Radachlorin®), Ru(II) polypyridyl complex (TLD-1433), padeliporfin di-potassium (TOOKAD®) and 5-aminolevulinic acid hydrochloride (Gliolan™, 5-ALA), among others known and yet to be developed. Just by way of example, the prescribed activation peak wavelength for Gliolan™ is 630 nm, Laserphyrin® is 664 nm, PHOTOFRIN® is 630 nm and HPPH-Photochlor is 665 nm. It should be noted that the prescribed activation peak wavelength can be achieved using embodiments of the present disclosure and that the therapy light delivered can have a nominal peak wavelength centered about the prescribed activation peak wavelength. The prescribed activation peak wavelength disclosed immediately herein above are but examples of the prescribed activation peak wavelengths that can be achieved using embodiments of the present disclosure and therapy light having other wavelengths can be delivered to match yet to be developed photosensitizing drugs as well as off label use as prescribed by a physician. In this way, embodiments of the present disclosure inventively enable a therapy light delivery system that can be configured to provide broad and accurate activation peak wavelengths.

Because cellular response to PDT is highly dependent on photosensitizer localization and site of activation, understanding and controlling photosensitizer localization can be used with methods of the present disclosure to elicit certain aforementioned effects and increase the potential therapeutic uses of configurable PDT system 20. The light targeting capability of configurable PDT system 20 enables the DLI at an optimum time prior to when the photosensitizing drug has cleared in healthy tissue, when the photosensitizer is in a desired location to be activated and to elicit the desired PDT effect. From the moment of administration, until the photosensitizer has reached the target location, various physical, chemical, and biological events take place over time that together influence the incubation and end location of the photosensitizer. This can be dependent on the pharmacokinetics of a particular photosensitizer and DLI, which can be adjusted for a desired end location using configurable PDT system 20 and the methods disclosed herein. Upon photosensitizer intravenous administration, it initially binds to serum proteins, and will associate and distribute differently based on its pharmacokinetics. The photosensitizer will then extravasate the blood vessels to reach the tumor site, and associate with the extracellular matrix and then cells within the tumor. As should be appreciated by those skilled in the art, photosensitizers have been shown to localize in numerous organelles and cellular compartments, its cellular uptake driven by structural characteristics of the drug molecule such as overall structure, charge and charge distribution, and lipophilicity that determine cellular uptake and subcellular localization of a photosensitizer that ultimately determine its therapeutic effect. In one example of a method that employs embodiments of the present disclosure, for a photosensitizing comprised of porfimer sodium, when therapy light of the appropriate wavelength after a DLI of three hours activates porfimer sodium in the plasma membrane and produces necrotic cell death. In this same example, after a 24 hour DLI the porfimer sodium is located in the in organelles, and therapy light of the appropriate wavelength produces apoptotic effects. Alternately, activating the photosensitizer with a short DLI prior to extravasation, typically one hour for most porphyrin-based photosensitizers, will result in vascular effects in which acute vascular response can be seen.

It has been discovered that with knowledge of a given photosensitizer pharmacokinetics, its uptake in a disease state, tissue type and a patient's specific biometrics, the targeted PDT light delivery of configurable PDT system 20 enables prescribing a DLI that can be implemented prior to normal tissue clearance to activate the drug in a desired location for a desired effect. Furthermore, it has been discovered and disclosed herein that modulation of the therapy light dosimetry parameters can be modulated to further optimize the desired effect. Light fluence rate has also been shown to affect tumor oxygenation required for PDT efficacy, in which high fluence rates can be used to deplete ambient tumor oxygenation, causing hypoxia and limiting treatment effectiveness. A combination of parameters that are controllable by the configurable PDT system 20 of the present disclosure, such as that photochemical oxygen consumption is proportional to the product of the photosensitizer absorption coefficient, photosensitizer concentration, and light fluence rate can be used to optimize the efficacy of the PDT procedure. In other words, PDT efficiency in maintaining suitable tissue oxygenation can be optimized by adjusting the fluence rate using the light controller of configurable PDT system 20, where the photosensitizer parameters are fixed.

Figure 6:
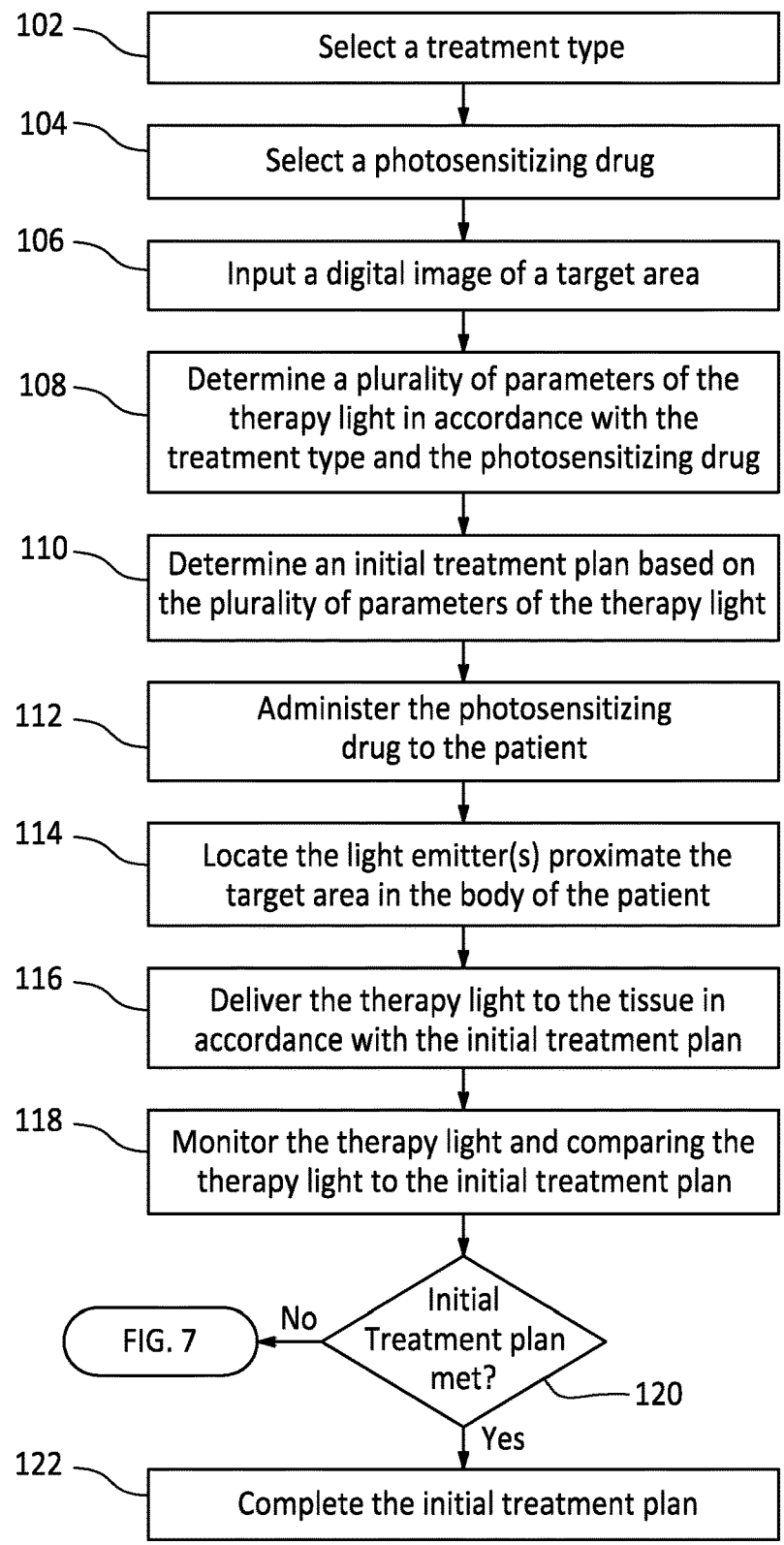
FIG. 6 is a flow chart of an operating procedure of a configurable PDT system in accordance the present disclosure.

Example methods of the present disclosure can best be shown with reference to FIG. 6 wherein the operating procedure 100 can be seen. At step 102 a user, or team of users, selects a treatment type to be performed the treatment type can include any type of PDT including necrotic, apoptotic, vascular, immunogenicity or immunoreactivity (treatments to provoke antitumor immune response) and other known PDT treatment type. The treatment type can be input into the computer processor in optical control instrument 21 or a standalone computer. At step 104 a user selects the type of photosensitizing drug to be administered which photosensitizing drug can include sodium porfimer (PHOTOFRIN®), talaporfin sodium (Laserphyrin®), 2-(1-Hexyloxyethyl)-2-Devinyl Pyropheophorbide-a (HPPH-Photochlor), benzoporphyrin derivative monoacid ring A (Verteporfin, Visudyne®), redaporfin (LUZ11), chlorin E6/P6/purpurin (Bremachlorin®, Radachlorin®), Ru(II) polypyridyl complex (TLD-1433), padeliporfin di-potassium (TOOKAD®) and 5-aminolevulinic acid hydrochloride (Gliolan™, 5-ALA), among others known or yet to be developed. At step 106 a user determines an initial therapy plan based on the input from steps 102, 104. The selected photosensitizing drug can be input into the computer processor in optical control instrument 21 or a standalone computer. At step 106 a digital image of the target area is input into the computer processor in optical control instrument 21 or a standalone computer. The digital image can be a CAT scan, an MRI, an x-ray or other suitable digital image. The target area can be of a gross tumor, a tumor bed of a resected tumor or fluoresced image of tumor cells. Based on the selected treatment type and the selected photosensitizing drug and the digital image of the target area the computer processor determines a plurality of parameters for the administration of therapy light to the target area at step 108. The appropriate selection of the light emitters to provide the irradiance pattern is an important factor. In certain embodiments of the present disclosure optical applicator 23 (FIG. 2) includes a plurality of light emitters which can comprise cylindrical light diffusers, segmented cylindrical light diffusers, point light diffusers and the like. One important parameter is the determination of which of the plurality of light emitters in optical applicator 23 to illuminate to produce an irradiance pattern that closely matches the digital image. This parameter can employ artificial intelligence methods and may include the operation of optical switches and multiple light sources to determine the irradiance pattern. This parameter can also include algorithms to provide a margin around the periphery of the digital image to ensure complete treatment of the target area. Another parameter is the selection of the proper wavelength of therapy light to match the photosensitizing drug selected in step 104. This parameter can be controlled by tuning a tunable light source to the appropriate wavelength or using optical switches to optically couple to a source having the appropriate wavelength within optical control instrument 21. Dosing is another parameter among the plurality of parameters for the administration of therapy light to the target area at step 108. Dosing includes determining the appropriate fluence rate ($mW/cm^2$), modulation (FIG. 5) and total fluence ($J/cm^2$) of therapy light to administer to the target area. At step 110 an initial treatment plan is determined which includes the output of step 108 and, as disclosed herein above, the optimum drug-light interval to elicit the proper effect to produce the selected treatment type among other parameters included in the initial treatment plan. The initial treatment plan can comprise a set of instructions in computer code to be run on the computer processor in optical control instrument 21 to operate the light controller, light source(s), detector and other components to execute the treatment plan. At step 112, the selected photosensitizing drug is administered to the patient by a user.

In accordance with an embodiment of a method for delivering light therapy to a patient of the present disclosure, the light emitters are located near the target area of a patient in step 114. It is contemplated in some embodiments that methods include the in vivo placement light emitters during an interoperative procedure. In an embodiment where a flexible optical applicator 23 is used, the optical applicator can include a first radiological marker that can be used in conjunction with digital images to accurately spatially locate the optical applicator with respect to the target area. After a surgical procedure to remove a gross tumor has been completed, a second radiological marker can be placed on the target area to be treated with the configurable PDT system 20. A preprocedural image can be acquired to determine the target area and the position of the second radiological marker relative to the target area. Aligning the first marker and the second marker the optical applicator 23 is placed proximate the target area inside the body of the patient. An intraprocedural image can be acquired to check the alignment of the first marker and the second marker. If there an offset distance exists, the optical applicator can be repositioned by moving it the offset distance such that the first marker and the second marker are aligned. Once the requisite DLI has passed, at step 116 the initial treatment plan is commenced, and therapy light is delivered to the target area using configurable PDT system 20. During the application of therapy light detectors within optical applicator 23 are used to monitor the dosing of therapy light and the computer processor compares the monitored therapy light with the treatment plan. Given that optical applicator 23 is a highly automated system and operates in a closed loop fashion, it is possible to deliver therapy light to the target area in strict accordance with the plan. In embodiments where the initial treatment plan is completed and the computer processor determines that initial plan is met at step 120, the PDT session is completed at step 122.

Figure 7:
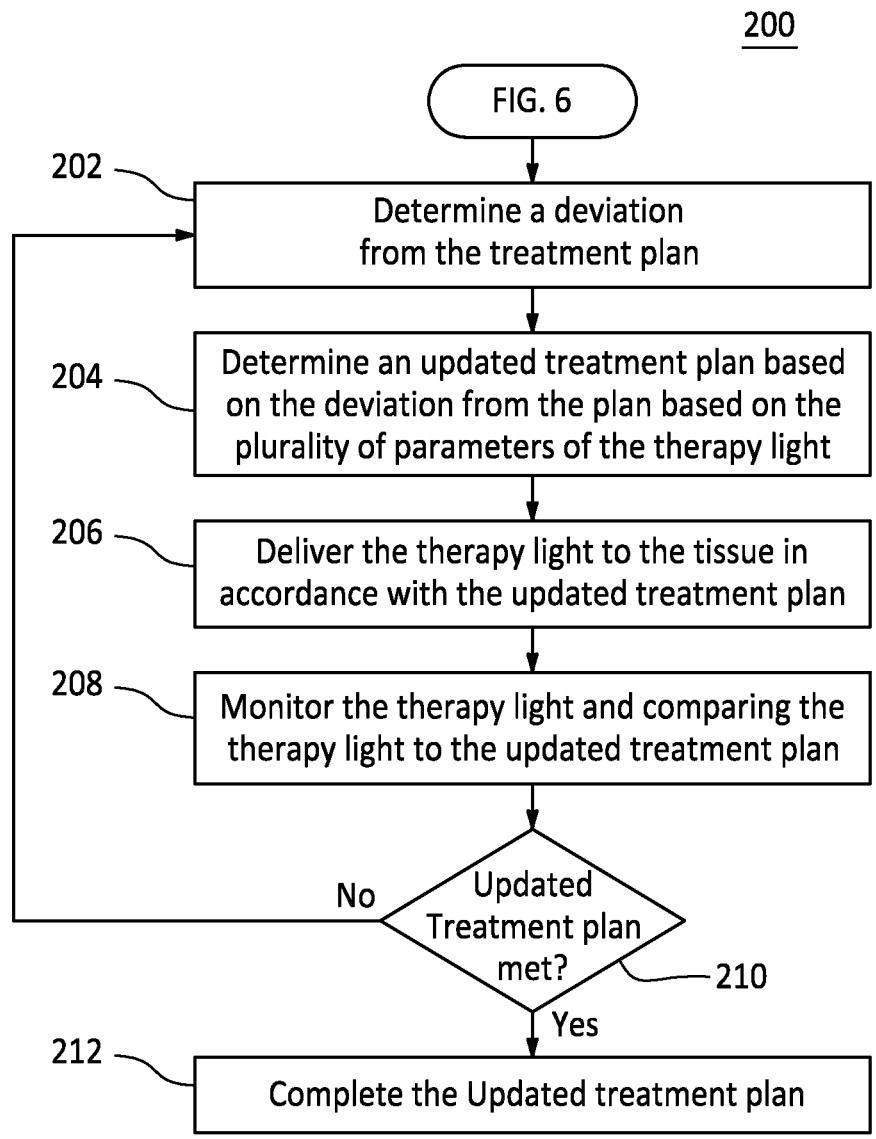
FIG. 7 is a flow chart of an operating procedure of a configurable PDT system in accordance the present disclosure.

With reference to FIG. 7, there is shown a method of the current disclosure wherein the operating procedure 100 (FIG. 6) deviated from the initial treatment plan in a way in which an updated treatment plan 200 must be executed to effectively treat the patient. The deviation from the initial treatment plan 100 is determined in step 202. Such differences can include a deviation from any of the plurality of parameters of therapy light in step 108, a deviation in the DLI, a power interruption, and the like. Inventively, optical control instrument 21 can determine the deviations and can further determine an updated treatment plan based on the deviation in step 204. Similar to steps 116 and 118, during the execution of updated treatment plan 200 therapy light is delivered to the target area using configurable PDT system 20 at step 206 and therapy light is monitored using a detection signal from detector fibers in the optical applicator 23 and the computer processor compares the monitored therapy light with the updated treatment plan in step 208. In embodiments where the updated treatment plan 200 is met as determined by the computer processor at step 210, the updated treatment plan is completed at step 212. In embodiments where the updated treatment plan 200 is not met as determined by the computer processor at step 210, steps 202-210 are repeated until the updated treatment plan is completed.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Although the invention(s) is/are described herein with reference to specific embodiments, various modifications and changes can be made without departing from the scope of the present invention(s), as presently set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated other The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

While the foregoing is directed to embodiments of the present invention, other and further embodiments of the invention may be devised without departing from the basic scope thereof, and the scope thereof is determined by the claims that follow.

What is claimed is:

1. A processor-implemented method to deliver a therapy light to a tissue of a patient, the processor-implemented method comprising:
   administering a photosensitizing drug to the patient;
   acquiring a preprocedural image of a surgical site, wherein the preprocedural image includes a first marker and a target tissue;
   providing a configurable photodynamic therapy system having a processor and a light emitting device, wherein the light emitting device includes a second marker;
   positioning the light emitting device against the target tissue with the second marker proximate the first marker;
   acquiring an intraprocedural image of the surgical site, wherein the intraprocedural image includes the first marker and the second marker;
   aligning the first marker and the second marker using the intraprocedural image,
   wherein aligning comprising determining a the distance between the first marker and the second marker and moving the light emitting device the distance between the first marker and the second marker to align the first mark and the second marker; and using the processor:
selecting a treatment type;
selecting the photosensitizing drug;
determining a plurality of parameters of the therapy light in accordance with the treatment type and the photosensitizing drug;
determining an initial treatment plan based on the plurality of parameters of the therapy light; and
delivering the therapy light to the target tissue in accordance with the initial treatment plan.

2. The processor-implemented method of claim 1 wherein the determining the plurality of parameters of the therapy light includes determining an irradiance pattern using the light emitting device and wherein the irradiance pattern matches either the preprocedural image or the intraprocedural image.

3. The processor-implemented method of claim 1 further comprising determining an optimum drug-light delivery interval based on the treatment type and the photosensitizing drug; and
wherein the determining the initial treatment plan further includes the optimum drug-light delivery interval.

4. The processor-implemented method of claim 1 wherein selecting the photosensitizing drug comprises selecting from the group consisting of porfimer (PHOTOFRIN®), talaporfin sodium (Laserphyrin®), 2-(1-Hexyloxyethyl)-2-Devinyl Pyropheophorbide-a (HPPH-Photochlor), benzoporphyrin derivative monoacid ring A (Verteporfin, Visudyne®), redaporfin (LUZ11), chlorin E6/P6/purpurin (Bremachlorin®, Radachlorin®), Ru(II) polypyridyl complex (TLD-1433), padeliporfin di-potassium (TOOKAD®) and 5-aminolevulinic acid hydrochloride (Gliolan™, 5-ALA).

5. The processor-implemented method of claim 1 wherein the photosensitizing drug includes a prescribed activation peak wavelength and wherein the delivering the therapy light to the target tissue further comprises controlling a light source to output the therapy light at a nominal peak wavelength centered about the prescribed activation peak wavelength.

6. The method of claim 5 wherein the photosensitizing drug comprises 2-(1-Hexyloxyethyl)-2-devinyl pyropheophorbide-a and controlling the light source to output the therapy light centered about a nominal peak wavelength of 665 nm.

7. The method of claim 5 wherein the photosensitizing drug type comprises porfimer sodium and controlling the light source to output the therapy light centered about a nominal peak wavelength of 630 nm.

8. The method of claim 5 wherein the photosensitizing drug type comprises talaporfin and the controlling the light source to output the therapy light centered about a nominal peak wavelength of 664 nm.

9. The method of claim 5 wherein the photosensitizing drug type comprises 5-aminolevulinic acid and controlling the light source to output the therapy light centered about a nominal peak wavelength of 630 nm.

10. The method of claim 1 wherein the determining the initial treatment plan further includes determining a duty cycle of the light emitting device.

11. The method of claim 1 wherein the determining the initial treatment plan further includes determining a fluence and a fluence rate of the light emitting device.

12. The method of claim 1 wherein the selecting a treatment type includes selecting from the group consisting of necrotic, apoptotic, vascular and immunogenicity.

* * * * *